United States Patent
Kroehnke et al.

(10) Patent No.: US 10,487,193 B2
(45) Date of Patent: Nov. 26, 2019

(54) STABILIZATION OF POLYAMIDES

(71) Applicant: CLARIANT PLASTICS & COATINGS LTD, Muttenz (CH)

(72) Inventors: Christoph Kroehnke, Breisach (DE); Matthias Zaeh, Gersthofen (DE)

(73) Assignee: Clariant Plastics & Coatings Ltd, Muttenz (CH)

( * ) Notice: Subject to any disclaimer, the term of this patent is extended or adjusted under 35 U.S.C. 154(b) by 0 days.

(21) Appl. No.: 15/541,975

(22) PCT Filed: Dec. 18, 2015

(86) PCT No.: PCT/EP2015/080547
§ 371 (c)(1),
(2) Date: Jul. 6, 2017

(87) PCT Pub. No.: WO2016/110397
PCT Pub. Date: Jul. 14, 2016

(65) Prior Publication Data
US 2018/0022896 A1    Jan. 25, 2018

(30) Foreign Application Priority Data
Jan. 7, 2015   (DE) .................. 10 2015 000 124

(51) Int. Cl.
*C08K 5/3435* (2006.01)
*C08K 5/3462* (2006.01)
(Continued)

(52) U.S. Cl.
CPC .......... *C08K 5/3435* (2013.01); *C07D 405/14* (2013.01); *C08K 5/3462* (2013.01)

(58) Field of Classification Search
CPC ..... C08L 77/02; C08K 5/3435; C08K 5/3462; C08K 5/3535; C08K 5/357; C07D 405/14
See application file for complete search history.

(56) References Cited

U.S. PATENT DOCUMENTS

| 4,378,443 A * | 3/1983 | Minagawa ........... C07D 519/00 |
| | | 524/102 |
| RE31,343 E * | 8/1983 | Holt ..................... C07D 211/46 |
| | | 546/188 |

(Continued)

FOREIGN PATENT DOCUMENTS

| EP | 776887 B1 | 3/2000 |
| EP | 1556350 B1 | 8/2007 |

(Continued)

OTHER PUBLICATIONS

International Search Report issued in corresponding International Patent Application No. PCT/EP2015/080547 dated Mar. 18, 2016.
(Continued)

*Primary Examiner* — Satya B Sastri
(74) *Attorney, Agent, or Firm* — Morgan, Lewis & Bockius LLP

(57) ABSTRACT

The invention relates to a method for stabilization of polyamides, which comprises admixing the polyamides before or during processing with an effective amount of one or more compounds of formula (1)

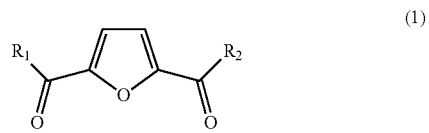

(1)

where $R_1$ and $R_2$ each represent a sterically hindered cyclic amine.

10 Claims, 1 Drawing Sheet

(51) Int. Cl.
*C08L 77/00* (2006.01)
*C07D 405/14* (2006.01)

(56) References Cited

U.S. PATENT DOCUMENTS

| | | | |
|---|---|---|---|
| 5,773,622 A | 6/1998 | Jegelka et al. | |
| 7,632,949 B2 * | 12/2009 | Mehrer | C08K 5/3435 |
| | | | 546/187 |
| 2011/0092720 A1 | 4/2011 | Yutaka et al. | |
| 2012/0283542 A1 * | 11/2012 | McGarraugh | A61B 5/14532 |
| | | | 600/365 |
| 2016/0251479 A1 * | 9/2016 | Smith | C08G 69/265 |
| | | | 524/607 |

FOREIGN PATENT DOCUMENTS

| | | | |
|---|---|---|---|
| WO | WO-9743335 A1 * | 11/1997 | C08G 69/48 |
| WO | 2004/016591 A1 | 2/2004 | |
| WO | 2011/043661 A1 | 4/2011 | |
| WO | 2015/014465 A1 | 2/2015 | |

OTHER PUBLICATIONS

Written Opinion issued in corresponding International Patent Application No. PCT/EP2015/080547 dated Mar. 18, 2016.

* cited by examiner

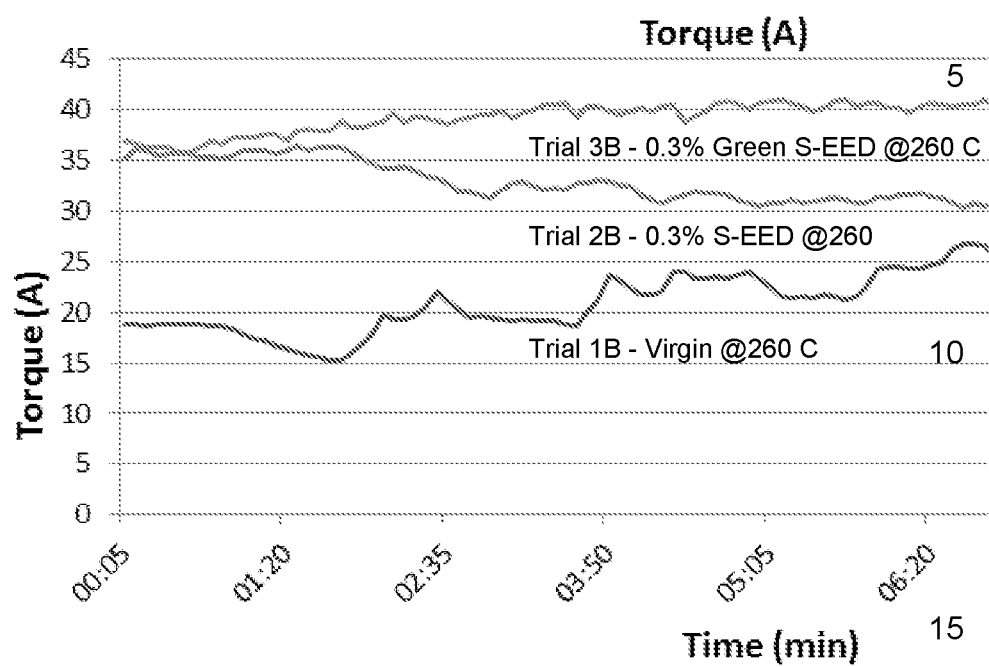

STABILIZATION OF POLYAMIDES

FIELD OF THE DISCLOSURE

The present invention relates to a method of enhancing the heat resistance, the light resistance and the chemical resistance of polyamides.

The present invention also relates to a composition of a stabilizer masterbatch and also to modified polyamides obtainable by said method.

BACKGROUND

Synthetic polyamides are typically processed at temperatures around 270° C. or above, particularly in spinning processes. Heat resistance issues can arise at these temperatures in that polyamides are decomposed by the heat. Further deficiencies of polyamides often include their poor resistance to light, their poor stability in melt processing due to their susceptibility to oxidation, their poor thermal aging and their poor resistance to chemical and oxidative agencies.

Sterically hindered cyclic amines are widely used in industry as stabilizers of polymers. Starting materials of particular interest include isophthalic acid and aromatic derivatives which are used for preparing N,N'-bis(2,2,6,6-tetramethyl-4-piperidinyl)-1,3-benzenedicarboxamide or other sterically hindered cyclic amine derivatives. 4-Amino-2,2,6,6-tetramethylpiperidine (TAD) is a typical building block of what are known as HALS systems. TAD is obtainable in a continuous manner on a large industrial scale as described in EP0776887 B1 for example.

EP 1556350 B1 describes an optimized process for preparing N,N'-bis(2,2,6,6-tetramethyl-4-piperidinyl)-1,3-benzenedicarboxamide.

However, the large scale industrial manufacture of the aromatic starting materials always proceeds from xylene, which is a petroleum derivative. Because petroleum sources are finite, it is advantageous to substitute "green" alternatives for this building block.

SUMMARY

The problem addressed by the present invention is therefore that of providing a method of enhancing the heat resistance, the light resistance and the chemical resistance of polyamides that uses additives formed from synthons that are at least partly obtainable from renewable raw materials and produce corresponding stabilizing effects in polyamides.

The problem addressed by the present invention was further that of providing stabilization masterbatches comprising such additives.

The problem addressed by the present invention was further that of providing correspondingly stabilized polyamides.

BRIEF DESCTION OF THE DRAWINGS

The FIGURE is a graph of torque during extrusion at T=260° as a function of time for three samples—Trail 1B, Trail 2B and Trial 3B.

DETAILED DESCRIPTION

It was found that, surprisingly, the divalent aromatic carbonyl compound 2,5-furandicarboxylic acid (FDCA) is useful as a building block for sterically hindered piperidine compounds and has the desired stabilizer properties in polyamides. FDCA is obtainable from 5-hydroxymethylfurfural (5-HMF) by suitable methods, for example as described in WO 2011/043661 A1 or US-2011/0092720 A1. 5-HMF is obtainable from renewable raw materials.

The invention accordingly provides a method for stabilization of polyamides, which comprises admixing the polyamides before or during processing with an effective amount of one or more compounds of formula (1)

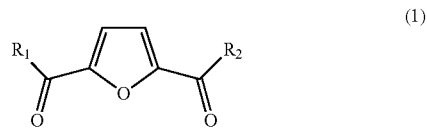

(1)

where $R_1$ and $R_2$ each represent a sterically hindered cyclic amine.

The moieties $R_1$ and $R_2$ each preferably conform to formula (2a), (2b) or (2c)

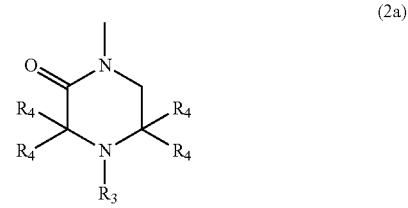

(2a)

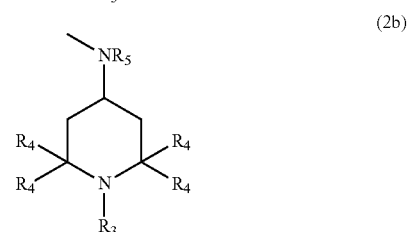

(2b)

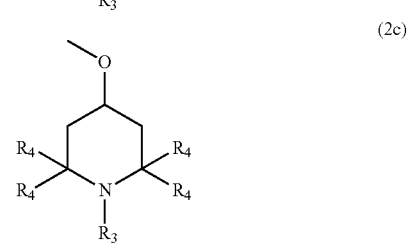

(2c)

where
$R_3$ is H, $C_1$-$C_5$ alkyl or $C_1$-$C_{10}$ alkoxy,
$R_4$ is H, $C_1$-$C_4$ alkyl or $C_6$ cycloalkyl, and
$R_5$ is H or $C_1$-$C_4$ alkyl.
$R_3$ is preferably H or $C_1$-$C_2$ alkyl, in particular H.
$R_4$ is preferably $C_1$-$C_2$ alkyl, in particular methyl.
$R_5$ is preferably H or methyl, in particular H.

Of particular interest are compounds of formula (1) where $R_1$ and $R_2$ are the same or different and are each a moiety of formula (2d), (2e) or (2f)

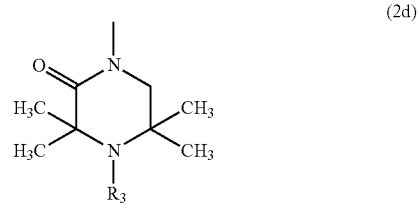

(2d)

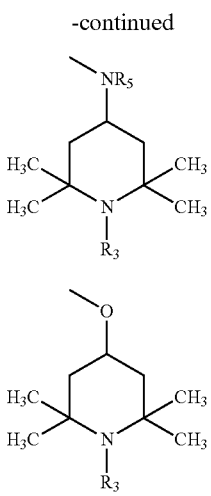

where $R_3$ and $R_5$ are each as defined above.

Of very particular interest are compounds of formula (1) where $R_1$ and $R_2$ are the same or different and are each a moiety of formula (2e) or (2f), for example the compounds N,N'-bis(2,2,6,6-tetramethyl-4-piperidinyl)-2,5-furandicarboxamide and N,N'-bis(2,2,6,6-tetramethyl-4-piperidinyl) 2,5-furandicarboxylate.

Compounds of formula (1) are obtainable by condensation of 2,5-furandicarbonyl dichloride or 2,5-furandicarboxylic esters with two equivalents of sterically hindered cyclic amine of the formula H—$R_1$ and/or H—$R_2$, as described in the as yet unpublished application PCT/EP2014/002034.

The addition of an effective amount of the above-described additive to polyamides, in particular synthetic polyamides, enhances the heat resistance, the light resistance and the chemical resistance in the polyamides without impairing other desired physical properties of the polyamide, for example the relative viscosity and the degree of polymerization. The polyamide thus additized further displays a low tendency to yellow and has higher extensibility and tenacity.

The additive of formula (1) is advantageously added to the polyamide in an amount of from 0.05 to 10.0 wt %, preferably of from 0.1 to 5.0 wt %, more preferably of from 0.2 to 2.5 wt %, in particular of from 0.25 to 1.0 wt %, based on the overall weight (100 wt %) of the stabilized polyamide.

The polyamide to be stabilized may be a homopolyamide, a copolyamide, a mixture of polyamides or a mixture between a polyamide and one or more other polymers.

Preference is given to homopolyamides and/or copolyamides obtainable from omega-aminohexanoic acid, omega-aminoheptanoic acid, omega-aminooctanoic acid, omega-aminopelargonic acid, omega-aminodecanoic acid, omega-aminoundecanoic acid, omega-aminolauric acid, caprolactam, lactam-7, lactam-8, lactam-9, lactam-10, lactam-11 and/or laurolactam.

The polyamides to be stabilized are also obtainable from diamines of the group dimethylenediamine, trimethylenediamine, tetramethylenediamine, pentamethylenediamine, hexamethylenediamine, polyether diamine, and also mixtures thereof, and dicarboxylic acids from the group oxalic acid, malonic acid, succinic acid, glutaric acid, adipic acid, pimelic acid, suberic acid, azelaic acid, sebacic acid, nonanedicarboxylic acid, decanedicarboxylic acid, undecanedicarboxylic acid, dodecanedicarboxylic acid, dimerized fatty carboxylic acids and also mixtures thereof.

The present invention further provides a stabilizer masterbatch comprising from 5 to 95 wt %, preferably from 10 to 90 wt %, more preferably from 20 to 80 wt %, in particular from 30 to 70 wt % of one or more compounds of formula (1) and from 95 to 5 wt %, preferably from 90 to 10 wt %, more preferably from 80 to 20 wt %, in particular from 70 to 30 wt % of a thermoplastic carrier polymer. The thermoplastic carrier polymer is identical to or at least compatible with the polyamide to be stabilized, and preferably is a polyamide. The stabilizer masterbatch is obtainable by mixing the individual constituents, preferably in powder or pellet form, and optionally by melting together and subsequent pelletization.

The stabilized polyamides are obtainable, for example, by mixing the additive of formula (1) or the above-described stabilizer masterbatch with the polyamide in a suitable container, for example in an extruder or kneader, before or during the melting or spinning, or before or during the polycondensation process of the polyamide itself, with or without a subsequent pelletization, spinning or shaping process.

Shaping processes include, for example, extrusion processes, injection molding, blow molding, calendering, in particular blown film extrusion, pipe/profile extrusion.

The present invention further provides a stabilized polyamide comprising at least one compound of formula (1), advantageously in an amount of from 0.05 to 10.0 wt %, preferably from 0.1 to 5.0 wt %, more preferably from 0.2 to 2.5 wt %, in particular from 0.25 to 1.0 wt %, based on the overall weight (100 wt %) of the stabilized polyamide.

The stabilized polyamide may be a powder, a pellet, a fiber or any desired shaped article, for example a self-supporting film/sheeting, a container, an injection molded article, a pipe or a profile.

The stabilized polyamide of the present invention may additionally comprise further customary stabilizing agents, for example antioxidants, light stabilizers, in particular HALS compounds and UV absorbers.

SYNTHESIS EXAMPLES

Synthesis Example 1: N,N'-Bis(2,2,6,6-tetramethyl-4-piperidinyl)-2,5-furandicarboxamide 10 ml (57.1 mmol, 2.2 eq) of 4-amino-2,2,6,6-tetramethylpiperidine are dissolved in 40 ml of N-methylpyrrolidone at room temperature and the solution is cooled to 0° C. 5.0 g (25.9 mmol) of 2,5-furandicarbonyl dichloride are added in multiple portions. The exothermic reaction results in the formation of a finely divided light-colored precipitate in the reaction mixture, which is stirred for one hour at 25° C. and for a further 4 hours at 100° C. After cooling, the mixture is poured into cyclohexane, and the precipitated product is filtered off, repeatedly washed with cyclohexane and dried.

Yield: 12.9 g of bispiperidinium dihydrochloride salt.

The free base (bispiperidine) is prepared by dissolving 6.7 g of bispiperidinium dihydrochloride salt in warm distilled water and adjusting the solution to pH 11.5 with 25 wt % aqueous ammonia solution. The colorless precipitate formed is filtered off and washed with water. Yield after drying: 4.9 g (11.3 mmol, 84% of theory) as colorless, crystalline, odorless solid material, melting point 240° C.

Synthesis Example 2: N,N'-Bis(2,2,6,6-tetramethyl-4-piperidinyl) 2,5-furandicarboxylate In a glass flask fitted with distillation head, 10.1 g (37.6 mmol) of dibutyl 2,5-furandicarboxylate, 15.1 g (95.6 mmol, 2.5 eq) of 4-hydroxy-2,2,6,6-tetramethylpiperidine and 300 µl of tetrabutyl titanate are heated to 150° C. under agitation and a slow stream of nitrogen to form a clear melt. Butanol begins to distill off after a short time. The temperature is raised to 180° C. in the course of 4 hours. After cooling, the cold melt is taken up with toluene and the included titanium compound is precipitated hydrolytically. Finally, the solvent is distilled off in vacuo. The crude product is purified by chromatography.

$R_f$=0.84 (3:1 methanol/dichloromethane).

Synthesis Example 3

5 g (27.2 mmol) of dimethyl 2,5-furandicarboxylate are dissolved in 50 ml of xylene under agitation and 9.3 g (59.8 mmol, 2.2 eq) of 3,3,5,5-tetramethyl-2-piperazinone are added. The mixture is heated to 60° C. and 2.5 ml of a 30 wt % sodium methoxide solution in methanol are added. The mixture is heated to 110-120° C. for 5 hours, and methanol distills off. Evaporation to dryness in vacuo leaves a yellowish powder which is triturated with ethyl acetate, filtered and dried.

Usage Examples

"S-EED":

N,N'-Bis(2,2,6,6-tetramethyl-4-piperidinyl)-1,3-benzenedicarboxamide (comparative);

"Green S-EED":

Inventive additive from synthesis example 1.

A) Preparation of Test Samples:

Nylon-6 ("Ultramie B27 E 01"; from BASF) was used as test substrate. Before being used to prepare the test specimens, the polyamide was comminuted with a grinding system (from Pallmann) at maximum grinding system speed. The additives were mixed with the polyamide powder in powder form or in the form of a pulverulent stabilizer masterbatch (60 wt % in nylon-6) using a Kenwood blender at slow speed of rotation for 5 minutes. Batch sizes were 0.8-1.5 kg. The additives were admixed in an amount so as to establish the hereinbelow reported final concentrations in the stabilized polyamide.

The pulverulent overall formulations were each dried for 12 hours in an evacuatable oven (from Binder) at 80° C. under controlled conditions to moisture levels of <0.1 weight percent. After cooling, nitrogen was introduced before the samples were used for compounding, for the production of injection molded plaques (see hereinbelow) and also for production of nylon-6 fibers (see hereinbelow).

A twofold pre-extrusion (first and second part) was carried out in a Collin single-screw extruder (30×25D; screw diameter 30 mm, two screw elements conveying, one pressure-relieving; L/D=5; diameter of exit slot 3 mm; rotary speed of screw 65/min, continuous measurement of torque) equipped with a water bath.

| First part Barrel temperatures | | | | | |
|---|---|---|---|---|---|
| Feed zone --------------------------------------------------> Exit | | | | | |
| Zone 1 | Zone 2 | Zone 3 | Zone 4 | Zone 5 | Zone 6 |
| 224° C. | 236° C. | 236° C. | 240° C. | 240° C. | 240° C. |

| Second part Barrel temperatures | | | | | |
|---|---|---|---|---|---|
| Feed zone --------------------------------------------------> Exit | | | | | |
| Zone 1 | Zone 2 | Zone 3 | Zone 4 | Zone 5 | Zone 6 |
| 233° C. | 241° C. | 245° C. | 260° C. | 260° C. | 260° C. |

Pelletization was run at maximum speed.

Pre-extrusion was used to investigate the influence of the additives on the individual formulations and on the throughput by measuring the torque.

B) Determination of Torque in Extrusion:

It transpired that unstabilized nylon-6 led to undesirable fluctuations in pressure at the exit die. These fluctuations were virtually completely eliminated on adding the inventive additives. Regarding torque at T=260°, the formulation comprising an inventive compound had higher and more constant values, as is apparent from the Figure.

C) Determination of Throughput in Extrusion:

Advantages from using the formulations comprising the inventive compound were also evident in relation to throughput. As table 1 shows hereinbelow, this holds not only at extrusion temperatures of 240° C. but also at 260° C.:

TABLE 1

| Formulation | Extrusion temperature [° C.] | Throughput [g/10 min] |
|---|---|---|
| Virgin | 240 | 936 |
| 0.3% S-EED | 240 | 970 |
| 0.3% Green S-EED | 240 | 978 |
| Virgin | 260 | 333 |
| | | (temporarily blocked) |
| 0.3% S-EED | 260 | 1000 |
| 0.3% Green S-EED | 260 | 1009 |

D) Weathering and Light Exposure Tests

The discoloration of test samples after weathering (long-term test) is one test criterion for light-induced degradation of polyamides. The long-term stability to light-induced degradation can be investigated via an accelerated, standardized test in a weatherometer (WOM). To this end, test samples are prepared with a defined geometry and then subjected to the weathering tests.

Production of Test Plaques by Injection Molding

Various additives (composition see table 2) were incorporated in nylon-6 as described above and processed on an Allrounder 320K injection molding machine (from Arburg) into injection molded plaques (thickness 1 mm).

The individual machine parameters were as follows:

injection temperatures: entry zone 270° C., zones 2-4: 280° C.; exit zone 295° C.

metering volume 21.5 cm$^3$ injection rate 3.5 cm$^3$/s injection pressure 2000 bar holding phases: 0.5 s each; holding pressure 1: 2200 bar, holding pressure 2: 25 bar temperature of compression mold: 80° C.

cooling time: 30 s

Conduct of Weathering Tests

The weathering tests were carried out in accordance with DIN 53 387-A.

The test criterion used was the development of color ("Yellowness Index"=YI).

The results are summarized hereinbelow in table 2:

TABLE 2

Stabilization of nylon-6 against light-induced degradation in Weather-Ometer (WOM) as per DIN 53 387-A (7000 h weathering)

| Stabilizer formulation [wt %] | Yellowness Index [YI] |
|---|---|
| none | brittle fracture after 2000 h |
| 0.30% Hostavin N20, 0.50% Hostavin ARO 8 | 5.3 |
| 0.30% Nylostab S-EED, 0.50% Hostavin ARO 8 | 4.0 |
| 0.30% "Green S-EED", 0.50% Hostavin ARO 8 | 3.7 |

Hostavin N20:

2,2,4,4-Tetramethyl-7-oxa-3,20-diazadispiro-(5.1.11.2)-heneicosan-21-one Hostavie ARO 8:

2-Hydroxy-4-n-octyloxybenzophenone

The inventive furan-analogous "S-EED" compound ("Green S-EED") from synthesis example 1 leads to less yellowing of the sample specimen after weathering than the comparative formulations.

Production, Finishing and Exposure of Nylon-6 Fibers

The nylon-6 samples used for fiber production contained 0.30 wt % of Nylostab S-EED (comparative) or 0.30 wt % each of inventive compounds from synthesis examples 1 to 3. The fibers were produced in a twin screw extruder with spinneret attachment at a temperature of 290° C. The pressure at the spinneret die was 100+/−3 bar. After emerging from the spinneret die, the fibers were subjected to an airstream at a temperature of 19+/−2° C., a relative humidity of 85% and a flow rate of 0.2+/−0.02 m/s. The fiber bundles were finally transported into a water bath containing a spin finish of the Fasavie 2733 type in a concentration of 15%. After drying, the fibers were wound up on supports with a winding apparatus at increasing speed (4200-4800-5400 m/min) and the wound packages were transferred into a weathering instrument ("Weather-Ometer"=WOM) and exposed therein for 4000 hours. On completion of the weathering time, the fibers were individually unwound. Their tenacity was determined by a method according to DIN 53455. The results are reported in table 3.

TABLE 3

Exposure of nylon-6 fibers in weathering instrument (Weather-Ometer = WOM) (4000 h weathering)

| Stabilizer formulation [wt %] | Tenacity [cN/tex] |
|---|---|
| 0.30% Nylostab S-EED | 38 |
| 0.30% "Green S-EED" | 43 |
| 0.30% from synthesis example 2 | 41 |
| 0.30% from synthesis example 3 | 40 |

What is claimed is:

1. A method for the stabilization of at least one polyamide, comprising the step of admixing the at least one polyamide before or during processing with an effective amount of one or more compounds of formula (1)

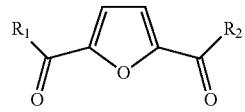

wherein $R_1$ and $R_2$ are the same or different and are each of the formula (2a) or (2b)

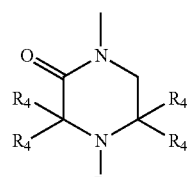

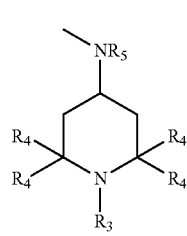

wherein $R_3$ is H, $C_1$-$C_5$ alkyl or $C_1$-$C_{10}$ alkoxy;

$R_4$ is H, $C_1$-$C_4$ alkyl or $C_6$ cycloalkyl; and $R_5$ is H or $C_1$-$C_4$ alkyl.

2. The method as claimed in claim 1, wherein the admixing step forms at least one stabilized polyamide having increased heat resistance, light resistance, chemical resistance or a combination thereof.

3. The method as claimed in claim 1, wherein $R_1$ and $R_2$ are the same or different and are each of the formula (2d) or (2e)

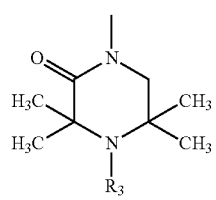

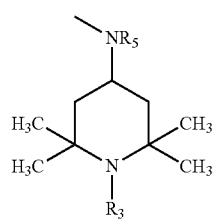

wherein $R_3$ is H or $C_1$-$C_2$ alkyl, and $R_5$ is H or methyl.

4. The method as claimed in claim 1, wherein the admixing step further comprises adding the compound of formula (1) to the at least one polyamide in an amount of 0.05 to 10.0 wt %, based on the overall weight (100 wt %) of the at least one stabilized polyamide.

5. The method as claimed in claim 1, wherein the admixing step further comprises adding the compound of formula (1) to the at least one polyamide in an amount of 0.25 to 1.0 wt %, based on the overall weight (100 wt %) of the at least one stabilized polyamide.

6. The method as claimed in claim 1, wherein the at least one polyamide is a homopolyamide, a copolyamide, a mixture of polyamides or a mixture between a polyamide and one or more other polymers.

7. The method as claimed in claim 1, wherein the admixing step further comprises mixing the one or more compounds of formula (1) with the at least one polyamide in an extruder or kneader, before or during the melting or spinning, or before or during the polycondensation process of the at least one polyamide, with or without a subsequent pelletization, spinning or shaping process.

8. The method as claimed in claim 1, wherein the one or more compounds of formula (1) is admixed to the at least one polyamide in the form of a masterbatch.

9. A stabilized polyamide comprising at least one compound of formula (1)

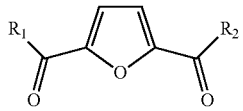
(1)

wherein $R_1$ and $R_2$ are the same or different and are each of the formula (2a) or (2b)

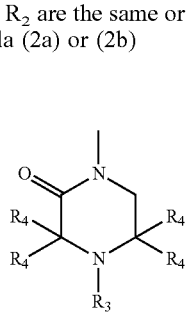
(2a)

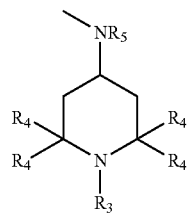
(2b)

wherein $R_3$ is H, $C_1$-$C_5$ alkyl or $C_1$-$C_{10}$ alkoxy;

$R_4$ is H, $C_1$-$C_4$ alkyl or $C_6$ cycloalkyl; and $R_5$ is H or $C_1$-$C_4$ alkyl.

10. The stabilized polyamide as claimed in claim 9, wherein $R_1$ and $R_2$ are the same or different and are each of the formula (2d) or (2e)

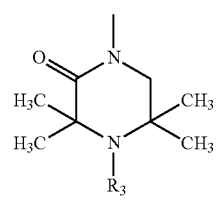
(2d)

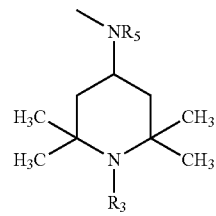
(2e)

wherein $R_3$ is H or $C_1$-$C_2$ alkyl, and $R_5$ is H or methyl.

* * * * *